(12) United States Patent
Cantrell

(10) Patent No.: US 9,034,310 B2
(45) Date of Patent: May 19, 2015

(54) INTERFERON-STATIN COMBINATION CANCER THERAPY

(76) Inventor: Stephen B. Cantrell, Franklin, TN (US)

(*) Notice: Subject to any disclaimer, the term of this patent is extended or adjusted under 35 U.S.C. 154(b) by 1108 days.

(21) Appl. No.: 10/370,434

(22) Filed: Feb. 20, 2003

(65) Prior Publication Data

US 2003/0232033 A1 Dec. 18, 2003

Related U.S. Application Data

(60) Provisional application No. 60/359,265, filed on Feb. 21, 2002.

(51) Int. Cl.
| | | |
|---|---|---|
| A61K 38/21 | (2006.01) | |
| C07K 14/555 | (2006.01) | |
| C07K 14/56 | (2006.01) | |
| C07K 14/565 | (2006.01) | |
| A61K 31/22 | (2006.01) | |
| A01N 43/38 | (2006.01) | |
| A61K 31/405 | (2006.01) | |
| A01N 37/10 | (2006.01) | |
| A61K 31/19 | (2006.01) | |

(52) U.S. Cl.
CPC .............. *A61K 38/212* (2013.01); *A61K 38/21* (2013.01); *A61K 38/215* (2013.01); *A61K 38/217* (2013.01)

(58) Field of Classification Search
None
See application file for complete search history.

(56) References Cited

U.S. PATENT DOCUMENTS

| | | | |
|---|---|---|---|
| 6,472,403 B2* | 10/2002 | Duggan et al. | 514/300 |
| 2002/0156122 A1* | 10/2002 | Mach | 514/423 |
| 2003/0170319 A1* | 9/2003 | Netke et al. | 424/682 |

OTHER PUBLICATIONS

Kawata S. et al. Effect of pravastatin on survival in patients with advanced hepatocellular carcinoma. A randomized controlled trial. 2001. Br. J. Cancer. vol. 84(7), p. 886-891.*
Minden, MD. et al. Lovastatin induced control of blast cell growth in an elderly patient with acue myeloblastic leukemia. 2001. Leukemia and Lymphoma. 2001. vol. 40, p. 659-662.*
Jonasch E. and Haluska, FG. Interferon in oncological practice: Review of interferon biology, clinical applications, and toxicities. 2001. The Oncologist. vol. 6, p. 34-55.*
Hasan J. and Jayson GC. VEGF antagonists. 2001. Expert Opin. Biol. Ther. vol. 1(4), p. 703-718.*
Yan L, et al. Dietary supplementation of selenomethionine reduces metastasis of melanoma cells in mice. Anticancer Research. 1999. vol. 19, p. 1337-1342.*
Soma M.R. et al. Simvastatin, an inhibitor of cholesterol biosynthesis, shows a synergistic effect with N.N.'-Bis(2-chloroethyl)-N-nitrosourea and B-interferon on human glioma cells. Cancer Research. 1992. vol. 52, p. 4348-4355.*
Zaidi, M.R. et al. The two faces of interferon-gamma in cancer. Clin. Cancer Res., 2011, vol. 17(19), p. 1-7.*

* cited by examiner

*Primary Examiner* — Robert Landsman
*Assistant Examiner* — Bruce D Hissong

(57) ABSTRACT

A method for pharmacological treatment of cancers and other diseases is presented which includes the novel combination of a statin (Hmg-CoA reductase inhibitor, such as lovastatin, simvastatin, atorvastatin, cerivastatin, fluvastatin, pravastatin, or newer agents), with an interferon (such as interferon alfa-2b or others) and also including concurrent administration of selenium and calcium. The method disclosed in this invention is useful because it can prove more effective than previously known therapies for certain diseases and because its use may be more tolerable, less disfiguring, and less expensive than other methods. The method here disclosed can be readily reproduced by any person skilled in the art of treating disease.

38 Claims, No Drawings

INTERFERON-STATIN COMBINATION CANCER THERAPY

CROSS-REFERENCE TO RELATED APPLICATIONS

This application claims the benefit of U.S. provisional patent application No. 60/359,265 mailed 20 Feb. 2002 and received for filing 21 Feb. 2002.

STATEMENT REGARDING FEDERALLY SPONSORED RESEARCH OR DEVELOPMENT

There has been no sponsorship or support from any agency of the United States government for any portion of the research producing this invention.

REFERENCE TO SEQUENCE LISTING, A TABLE, ETC.

Not applicable.

BACKGROUND OF THE INVENTION

The state of the art in cancer treatment is surgical resection, chemotherapy, and in some cases radiation therapy. In the case of the cancer known as melanoma, interferon is sometimes used as well. Such methods have serious drawbacks, chief among them a lack of effectiveness (which means that most patients still progress to death from disease), and severely incapacitating side effects and disfigurement. The many experimental methods also currently in use attest to the profound deficiency of the state of the art for treatment of most malignancies. In short, the whole world still eagerly seeks a cure for cancer. The present invention seeks to address these inadequacies by offering a novel treatment method which is more effective, more tolerable, less disfiguring, and ultimately less costly than existing methods.

BRIEF SUMMARY OF THE INVENTION

The current invention comprises the combination of interferons and mevalonic acid biosynthesis inhibitors (also known as Hmg-CoA reductase inhibitors, or "statins"), administered in conjunction with calcium and selenium. Both the interferons and the statins share some overlap in activity with a group of drugs useful for inhibiting the formation and maintenance of blood vessels, properly termed angiogenesis inhibitors but often called "angiostatins" after a representative example of these agents. The method described herein is believed to be potentially superior to currently known methods in that it actually is effective in the regression, eradication, or long-term suppression of many cancers, and may thus give hope of survival and may eventually prevent much of the disfigurement and side effects of less effective treatments. A preferred embodiment would involve daily oral administration of the Hmg-CoA reductase inhibitor (for example, lovastatin) and selenium and calcium, and periodic subcutaneous injection of interferon (for example, interferon alfa-2b) from one to three times each week; or a similar combination of the Hmg-CoA reductase inhibitor with an angiogenesis inhibitor (for example, thalidomide). Metastatic melanoma is a typical example of a life-threatening cancer that may be treated with this combination. The combination may also be used to treat other forms of cancer and other diseases, including certain infectious diseases.

BRIEF DESCRIPTION OF THE SEVERAL VIEWS OF THE DRAWING

Not applicable. No drawings are pertinent to understanding, making, and using the present invention.

DETAILED DESCRIPTION OF THE INVENTION

The novel treatment method of the present invention comprises a previously unknown combination of agents which, when administered together via the method here described, yield a significantly enhanced effectiveness against certain diseases as demonstrated in human patients.

The group of pharmacologic agents typically known as "statins" (also correctly known as 3-hydroxy-3-methylglutaryl enzyme-CoA reductase inhibitors, Hmg-CoA reductase inhibitors, HRI's, and mevalonic acid biosynthesis inhibitors) exist in several formulations which are approved for usage by humans for the primary purpose of beneficially altering serum lipid (cholesterol) levels and therefore lowering risk for vascular events such as myocardial infarction. Typical examples which are already available for prescription include lovastatin, simvastatin, pravastatin, fluvastatin, atorvastatin, and cerivastatin. It is also known in prior medical literature that some of these compounds may have some inhibitory effects on the growth of certain varieties of cancer cells in laboratory conditions; however in the very few attempts to apply these agents to human cancers there has been no appreciable benefit and it is generally believed that sufficient dosages to have benefit against cancer cannot be achieved without causing unacceptable or even lethal toxicity of the drugs themselves. There is also known a similar and sometimes overlapping group of compounds described as angiogenesis inhibitors, which are observed to inhibit the growth and maintenance of blood vessels. Thalidomide is an example of this group, along with others such as angiostatin, endostatin, amifostine, tumstatin, anginex, curcumin, and others. These two groups are not actually fully distinct, as the "statins" have also been demonstrated to interfere with angiogenesis. Some interferons have been shown to exert limited inhibition of angiogenesis as well.

Interferons refer to a group of chemically similar proteins which occur in many animal species including humans, in which a number of similar but distinct interferons naturally occur. Their functions in the human body are believed to include enhancing the effectiveness of the native immune system to combat viral infections and in some cases to inhibit cellular proliferation. Various interferons, chemically identical to certain of the interferons produced by the human body, have been produced via standard known recombinant techniques and are presently commercially available by a physician's prescription. These include such examples as interferon alfa-2a, alfa-2b, alfa-2c, alfa-n1, alfa-n3, and beta and gamma interferon groups. The actions of these chemically similar compounds are not fully known but are similar in many known respects. Interferon alfa-2b in particular is widely used to combat the infectious disease hepatitis C and has limited application in human immunodeficiency virus infection. It has also been approved for treatment of the cancer known as melanoma in certain cases, although analysis has shown relatively little benefit to most patients consisting primarily of a few months' delay in the progression to death.

To the best knowledge and belief of the inventor, there has been no prior description of the combination of a statin with an interferon for the treatment of disease. The present invention, comprising a method of treatment with a novel combination of a statin and an interferon or an angiogenesis inhibitor, with or without concurrent administration of nutrients such as selenium and calcium, has shown effectiveness in early human experience for the treatment of advanced cases of pancreatic cancer, malignant fibrous histiocytoma (a sarcoma), and the skin cancer melanoma in advanced metastatic stages. (As yet unpublished data based on inventor's personal experience.) All of these are well known as aggressive cancers in which death is virtually assured and often quite rapid. It is further anticipated that this invention may be useful in the treatment of other aggressive and deadly cancers and perhaps in other disease conditions including but not limited to serious viral infections.

EXAMPLE OF APPLICATION

Metastatic Melanoma

A preferred embodiment of this invention may be administered in the following manner by any person skilled in the art of treatment of disease. An example of a patient who may benefit from this invention is an adult with advanced metastatic melanoma. In this typical embodiment, a commercially available "over-the-counter" preparation of yeast-derived selenium will be administered orally in a dosage of two hundred micrograms daily. A commercially available "over-the-counter" preparation of calcium with vitamin D will be administered orally, separated from any other medication administration by at least one hour, in a dosage of at least 600 milligrams and not more than 1200 milligrams of elemental calcium daily. Lovastatin will be administered orally with meals, beginning with a dosage of twenty milligrams daily and gradually increasing over a period of two weeks until a target dosage has been reached consisting of a total daily dosage of 1.1 to 1.2 milligrams per kilogram of body weight, divided in three or four administrations each day. When the full desired dosage level of lovastatin has been reached, interferon administration will begin also. Interferon alfa-2b will be administered by injection (subcutaneous or intramuscular preferred) in a dosage of five million international units (or approximately 60,000 to 70,000 international units per kilogram of body weight) in each of three administrations per week. Once full dosages of all agents have been achieved as described, such treatment will continue until no further evidence of cancer can be demonstrated. In some cases this may be effected in as little as six weeks of full dose therapy. At this point reduced maintenance dosages will be instituted consisting of a total of 0.7 to 1.0 milligrams of lovastatin per kilogram of body weight daily divided in three or four doses with meals, two hundred micrograms of selenium daily, and five million international units (or approximately 60,000 to 70,000 international units per kilogram of body weight) of interferon alfa-2b injected once weekly. Calcium administration will also be continued at the same dosage level indefinitely. After one year of disease-free status, interferon dosage will be further reduced to three million international units (or approximately 35,000 to 45,000 international units per kilogram of body weight) once weekly while lovastatin and selenium dosages remain constant. If periodic monitoring ever indicates any cancer recurrence, the full regimen at highest dosage levels will resume. Throughout the course of treatment, the physician will monitor the patient for side effects of any of the agents used, and will periodically employ known methods such as computed tomography ("CT scan"), positron emission tomography ("PET scan"), blood assays and cell counts, or other methods known to be effective for detecting and evaluating the extent of the particular cancer.

This preferred embodiment may be further illustrated with the following example of an eighteen year old human female, weighing 55 kilograms, diagnosed with metastatic melanoma. The treatment will be divided into four phases designated as preparation, active treatment, ascertainment, and maintenance. Typical instructions for a physician or other person skilled in the art of treatment of disease administering the method in this example are given as follows.

EXAMPLE APPLICATION

Physician Instructions—Continued

Preparation Phase

1. Obtain the patient's consent for treatment after full discussion of relevant factors.

2. Patient must not be taking calcium channel blockers. If treatment of hypertension/angina/etc is required, alternative therapy must be instituted before this protocol may be initiated. When substitution is required, ACE inhibitors or other agents of physician's choice are recommended.

3. Patient must be warned not to ingest niacin supplements (other than the amount included in standard multivitamins), grapefruit, or any drink containing grapefruit juice.

4. Begin daily oral administration of selenium 200 mcg. Most over-the-counter formulations are acceptable; patient should be counseled to purchase a formulation which states that it is prepared from selenium yeast or Selenomax™ yeast. Evening administration is recommended and may be in conjunction with any other vitamins (eg, one-a-day multivitamins) the patient prefers to take.

5. Begin daily oral administration of calcium 600 mg with vitamin D. Most over-the-counter formulations are acceptable. The amount of elemental calcium supplied should be at least 600 mg and should not exceed 1200 mg daily. Calcium must not be taken at the same time as any other medication. Mid-morning administration is recommended (or with lunch if no medications are taken then), separated by at least one hour from any other agent.

6. Educate patient on proper techniques and sites for subcutaneous injection, and refrigerated storage and sterile handling of injectable agents.

7. The patient should purchase and keep in reserve a few capsules of coenzyme Q10 ("ubiquinone"). These should not be used. Further discussion follows.

The following steps are strongly recommended.

8. Baseline serum hepatic enzyme levels ("LFTs" for liver function tests) should be obtained as well as standard serum chemistry. If LFTs are more than twice normal upper limits, refer to inclusion criteria and use judgment whether to proceed. You may proceed if you deem the risk of untreated cancer to exceed the risk of medication side effects, or if the elevation is likely due to hepatobiliary obstructive effect of tumor mass.

9. Your chosen method of evaluating extent of this cancer (eg, CT scan, PET scan, cell counts, etc) should have been performed recently or should be repeated if not reasonably current. For solid tumors, positron emission tomography (PET) is strongly recommended. If PET has not been previously employed and you now elect to employ it, treatment should not be delayed for this reason. PET scans can be obtained as preparation and initial active treatment begins.

EXAMPLE APPLICATION

Physician Instructions—Continued

Active Treatment Phase

The specific method described in this example is customized and suitable for this patient only.

1. Prepare prescriptions for lovastatin 10 mg tabs, #30 for acclimation period; lovastatin 20 mg tabs, #90 or your preferred quantity for further treatment; interferon alfa-2b recombinant for injection; additional tuberculin syringes as will be required. Lovastatin may be prescribed as Mevacor™ (Merck) or as generic which became available December 2001 and is also acceptable. Interferon must be prescribed as Intron-A™, 10 million units/ml (Schering) in a 6-vial multi-pack known as "Pak-10." The unique NDC designation is 0085-1179-02 and you should make sure the pharmacy dispenses exactly this, as several other formulations are produced which are not suitable. Each Intron package includes alcohol wipes and six syringes. An additional six or more syringes will be needed with each package in this protocol.

2. A provision is made in this protocol for alternate use of simvastatin (Zocor™) for patients who are already taking it. Such modification can be made only with specific approval and revised dosage guidelines.

3. Administration of selenium and calcium continues as per guidelines above.

4. Lovastatin administration begins with an acclimation period toward a target dose of 60 mg daily. Lovastatin is always taken with food and separated from any other agent by at least thirty minutes (one hour minimum from calcium). When the schedule refers to "late afternoon," this is defined as administration between 3:00 and 6:00 pm which may be with an early dinner or a snack. Administration qhs should take place with a snack or glass of milk, etc. (Calcium effect is minimal in this small amount.) Acclimation takes place over twelve days as follows:

| Days | Dose | Schedule |
|---|---|---|
| Days 1–2 | 10 mg | evening meal |
| Days 3–4 | 20 mg | 10 mg breakfast, 10 mg evening meal |
| Days 5–6 | 30 mg | 10 mg breakfast, 10 mg late afternoon, 10 mg qhs |
| Days 7–8 | 40 mg | 10 mg breakfast, 10 mg late afternoon, 20 mg qhs |
| Days 9–10 | 50 mg | 20 mg breakfast, 10 mg late afternoon, 20 mg qhs |
| Days 11–12 | 60 mg | 20 mg breakfast, 20 mg late afternoon, 20 mg qhs |

If any doses are missed, they may be taken as soon as possible or at a schedule upon your advice. Once the target dosage has been reached as at days 11-12, this schedule will continue for the remainder of the active treatment phase.

5. Interferon administration begins on day 13 or 14 and will occur on the same three days each week, and at approximately the same time on each of these days, under your guidance. Any days may be chosen so long as there is never less than 48 hrs and never more than 72 hrs between injections. Injection in the middle to latter half of the evening (roughly between 7:00 and 10:00 pm for many patients) is helpful since the resulting fatigue and mild malaise will be timed to occur primarily during sleeping hours. Patients able to take ibuprofen (or other NSAID) will find it extremely helpful to take 400 to 600 mg about the same time the injection is given; it thus enters the system opportunely to minimize post-injection fever, headache, and chills. Acetaminophen may also be used but is not nearly as effective for many patients. Interferon dosage for this patient is as follows:

| | |
|---|---|
| First six injections | 5 million units (0.5 ml) per injection |
| Subsequent injections | 4 million units (0.4 ml) per injection |

Dosage will then remain constant for the remainder of the active treatment phase. Subcutaneous or intramuscular injection is preferred. Intravenous injection may greatly increase side effects and may diminish efficacy. If intravenous administration occurs inadvertently, the protocol remains valid and no additional dosage should be given.

6. The dosages detailed are strongly recommended without modification, and the patient should be counseled that response to the injections will become much more favorable after about two "rough" weeks due to:
   a. Decreasing dosages after the second week.
   b. The body's acclimation to the agent at these moderately high levels.
   c. Unpleasant initial physiologic effects which may be due to the sudden and simultaneous necrosis of large numbers of tumor cells early in treatment.

However, the following modifications may be made at your discretion, if you determine them medically necessary due to inability to tolerate full dosage:
   a. Interferon dosage may be reduced to 4 million units as of the third injection.
   b. Interferon dosage may be reduced to 3.5 million units as of the sixth injection.
   c. Interferon injection schedule may be reduced to twice per week after three full weeks of three injections each.

7. Repetition of serum chemistry and LFTs is recommended at day 12 (prior to initiation of interferon), again at two to three weeks after initiation of interferon, or at your discretion. An elevation in LFTs is expected, usually approximating one-and-a-half to two times upper limits. This is of little consequence; it is virtually always asymptomatic and experience shows that it is rare indeed for statins to cause hepatic impairment requiring cessation or reduction of dosing. Your judgment must prevail in weighing the risks of treatment vs non-treatment, but a laboratory finding in an asymptomatic patient must be evaluated in context and is not in itself sufficient reason to discontinue.

8. IMPORTANT: Your patient must be counseled appropriately and monitored for the extremely rare but serious side effect of myopathy or myolysis secondary to Hmg-CoA reductase inhibitor activity. The cautions and instructions in this regard are identical to those patients taking statins for the more typical indication of lipid control. In this protocol, it is important to educate the patient and to carefully catalog reported side effects so as not to confuse fatigue, malaise, and possible mild arthralgias ("flu-like" symptoms inevitable with interferon treatment) with actual statin-induced myopathy (very rare and presenting with extreme muscle tenderness and acute muscle pain). In the unlikely event that myopathy has occurred as determined by your judgment, the statin should be discontinued and the patient should be counseled to immediately consume 100 mg of coenzyme Q10 ("ubiquinone") and seek emergency medical treatment. Although the physician must be aware of the possibility of myopathy when treating any patient with a statin for any reason, it bears emphasizing that this occurrence is exceedingly rare and that expected interferon side effects are almost always the correct explanation for mild muscle and joint complaints. Under no circumstances should the patient make this determination. Should you initiate this plan, the presence or absence of myopathy will then be documented and treated appropriately. If myopathy is not present upon specific testing, the regimen may be resumed immediately. If the patient has not taken lovastatin for more than 48 hrs, treatment should resume with 40 mg and return to the full target dose of 60 mg under your direction over a period of four days.
9. If surgical treatment is anticipated or the patient withstands significant injury or inflammation, protocol modification may be necessary. The recommended change consists of cessation of lovastatin beginning one day before surgery until three days after surgery. Dosage may then resume at 40 mg and gradually increase back to the full target dosage over a period of two weeks. If impaired wound healing is evident, further cessation may be warranted.

EXAMPLE APPLICATION

Physician Instructions—Continued

Ascertainment Phase
1. Treatment effect will be evaluated after six full weeks of active treatment with all agents combined (ie, six weeks after initiation of interferon injections). The patient's current weight will be obtained.
2. The evaluation method most useful for this cancer (CT scan, PET scan, cell counts, etc) should once again be employed. Active treatment continues until results are evaluated.
3. Further action will be planned based upon results as follows:
   a. Evidence of malignancy can no longer be demonstrated: Active treatment will continue at full doses for an additional two weeks from the date of the test acquisition, and then proceed to maintenance phase.
   b. Significant benefit can be demonstrated, but malignancy is not yet eradicated: Active treatment will continue for an additional four to six weeks, at your discretion, and ascertainment phase will be repeated. (For example, a typical scenario is that lesions in soft tissue are completely or nearly eradicated at this point, and intraosseous metastases are significantly smaller but not yet eliminated.)
   c. Minimal benefit is evident: You may elect to continue active treatment and re-evaluate after four to six weeks, or continue active treatment and add a single chemotherapeutic agent of your choice. Preliminary evidence suggests a significantly enhanced effect of several agents (including 5-FU, cisplatin, and others) when combined with certain agents employed in this technique. This decision should be considered if little benefit can be appreciated from the standard protocol. Results will again be ascertained after four to six weeks under the modified protocol.
   d. No benefit can be demonstrated: You may elect to discontinue this protocol immediately and proceed to other treatment of your choice, or to continue active treatment and add a single chemotherapeutic agent as in item c above.
4. If the patient will be continuing active therapy or any variation of it as above, and the current weight is more than 5 kg different than the starting weight, dosages should be re-calculated based on the new weight.

EXAMPLE APPLICATION

Physician Instructions—Continued

Maintenance Phase
1. A regimen with specifically determined dosages (reduced and very tolerable) will be provided for the patient once clinically disease-free. It must be emphasized that data cannot yet support complete cessation of treatment.
2. After one year of documented disease-free status, a long-term maintenance regimen will be provided which has virtually no discernible side effects.
This concludes the example of applying the preferred embodiment in the treatment of metastatic melanoma.

While the embodiments described and the examples given above represent typical applications, they are simply my chosen means of illustration and do not limit the scope of application included in the present invention. To any physician or other person skilled in the art of treatment of disease, it will be obvious from this description that the present invention is also applicable in other embodiments or in conjunction with other known therapies which will include but are not limited to:
the use of other pharmacologic agents in the category of Hmg-CoA reductase inhibitors in lieu of or in addition to lovastatin, with dosages selected for therapeutic equivalency;
the use of other pharmacologic agents in the category of interferons in lieu of or in addition to interferon alfa-2b;
the use of other pharmacologic agents useful for inhibition of angiogenesis in lieu of or in addition to interferon;
the inclusion or omission of selenium;
the inclusion or ommission of calcium and other known nutrients;
further addition of other pharmacologic agents such as non-steroidal anti-inflammatory drugs, cyclo-oxygenase inhibitors, and nutrients;
adjustments of dosages, dosing intervals, and routes of administration of these agents;
application of the method to pediatric patients with corresponding adjustments of dosages, dosing intervals, and routes of administration of these agents;
application to cancers other than melanoma, including any cancer;
alternative methods of delivery or composition of any of these agents including but not limited to such methods and devices as "slow release" preparations for sustained or extended availability or delivery, continuous infusions, and direct surgical administration;
further alterations in dosages, dosing intervals, and routes of administration for long-term "maintenance" therapy;
further addition of agents or methods intended to enhance permeability of the blood-brain barrier or otherwise to achieve improved delivery of these agents to brain tissues;
further addition of agents or methods intended to achieve improved delivery of these agents to any other tissues or organs or cells;
composition of more than one agent in combined preparations for oral administration, injection, implantation, or other route of administration;
employment of this invention concurrent with other known methods of disease treatment including but not limited to chemotherapy, surgery, radiation, vaccines, agents and methods useful to inhibit cellular and intracellular signal transduction, agents and methods useful to disrupt viral replication and infection, and other methods;
application of these methods to non-human animals;
employment of this invention for disease entities other than cancers, including but not limited to such examples as hepatitis B and C, human immunodeficiency virus infection, viral warts, osteoporosis, autoimmune disorders, neuropathies, and any other disease state;
application of this method to cells or tissues outside the body which might then be re-introduced to the body of a patient.

Thus a number of applications and variations are anticipated in this invention and description as being obvious to the individual skilled in such art.

I claim:

1. A method of treating a mammal having cancer, said method comprising the administration of a therapeutically effective amount of one or more Hmg-CoA reductase inhibitors the one or more Hmg-CoA reductase inhibitors comprising one or more statin pharmacological agents, and a therapeutically effective amount of one or more interferons, other than gamma interferons, wherein said Hmg-CoA reductase inhibitors and interferons are administered to treat said cancer and reduce the likelihood of death caused by said cancer greater than by either the one or more Hmg-CoA reductase inhibitors or the one or more interferons administered alone.

2. A method according to claim 1 in which the one or more statin pharmacological agents employed may include one or more selected from the known group of lovastatin, simvastatin, pravastatin, fluvastatin, atorvastatin, cerivastatin, and any other statin pharmacological agents.

3. A method according to claim 1 wherein the one or more interferons employed may include one or more selected from the known group of interferon alfa-2a, alfa-2b, alfa-2c, alfa-n1, alfa-n3, beta interferon, any other pharmacologic agents classified as interferons, and combinations thereof.

4. A method of treating a mammal having cancer, comprising the steps of:
   a) providing a mammal having cancer;
   b) administering a gradually increasing dosage of one or more Hmg-CoA reductase inhibitors to the mammal until the dosage of the one or more Hmg-CoA reductase inhibitors reaches a desired dosage of the one or more Hmg-CoA reductase inhibitors based upon the bodyweight of the mammal, the one or more Hmg-CoA reductase inhibitors comprising one or more statin pharmacological agents;
   c) administering one or more interferons, other than a gamma interferon, in a dosage based upon the bodyweight of the mammal after reaching the desired dosage of the one or more Hmg-CoA reductase inhibitors; and
   d) continuing the administration of the one or more Hmg-CoA reductase inhibitors and the one or more interferons to treat said cancer and reduce the likelihood of death caused by said cancer greater than by either the one or more Hmg-CoA reductase inhibitors or the one or more interferons administered alone.

5. The method of claim 4 wherein the cancer is metastatic melanoma.

6. The method of claim 4 further comprising daily administration of selenium.

7. The method of claim 6 wherein the daily administration of selenium comprises a dosage of about 200 micrograms.

8. The method of claim 4 further comprising daily administration of calcium.

9. The method of claim 8 wherein the daily administration of calcium comprises a dosage of from about 600 milligrams to about 1200 milligrams.

10. The method of claim 4 wherein the one or more Hmg-CoA reductase inhibitors comprises lovastatin.

11. The method of claim 4 wherein the one or more Hmg-CoA reductase inhibitors are selected from the group consisting of lovastatin, simvastatin, pravastatin, fluvastatin, atorvastatin, cerivastatin, and any statin useful for the inhibition of activity of Hmg-CoA reductase and combinations thereof.

12. The method of claim 4 wherein step b) further comprises an initial dosage of about twenty milligrams of the one or more Hmg-CoA reductase inhibitors and gradually increasing the dosage to the desired dosage of the one or more Hmg-CoA reductase inhibitors over a period of about fourteen days.

13. The method of claim 4 wherein step b) further comprises an initial dosage of about twenty milligrams of the one or more reductase inhibitors and gradually increasing the dosage to the desired dosage of the one or more Hmg-CoA reductase inhibitors of about 1.1 to about 1.2 milligrams per kilograms of bodyweight of the mammal.

14. The method of claim 4 wherein step b) further comprises an initial dosage of about twenty milligrams of the one or more Hmg-CoA reductase inhibitors and gradually increasing the dosage to the desired dosage of the one or more Hmg-CoA reductase inhibitors of about 1.1 to about 1.2 milligrams per kilograms of bodyweight of the mammal over a period of about fourteen days.

15. The method of claim 4 wherein the dosage of the one or more interferons in step c) comprises of from about 60,000 international units to about 70,000 international units per kilogram of the body weight of the mammal with about three dosages of the one or more interferons administered per week.

16. The method of claim 4 further comprising:
   e) administering a maintenance dosage of from about 0.7 milligrams to about 1.0 milligrams of the one or more Hmg-CoA reductase inhibitors per kilogram of the bodyweight of the mammal per day and a dosage of from about 60,000 international units to about 70,000 international units per kilogram of the body weight of the mammal of the one or more interferons once per week.

17. The method of claim 16 wherein step e) further comprises a dosage of about 200 micrograms of selenium per day.

18. The method of claim 16 wherein step e) further comprises a dosage of from about 600 milligrams to about 1200 milligrams of calcium per day.

19. The method of claim 16 further comprising:
   f) reducing the maintenance dosage of the one or more interferons to about 35,000 international units to about 45,000 international units per kilogram of the bodyweight of the mammal after a period of about one year of absence of the cancer.

20. The method of claim 16 further comprising:
   g) increasing the dosages of the one or more interferons and the one or more Hmg-CoA reductase inhibitors if the cancer returns.

21. A method of treating a mammal with metastatic melanoma comprising the steps of:
   a) providing a mammal having metastatic melanoma;
   b) administering a gradually increasing dosage of a one or more Hmg-CoA reductase inhibitors, the one or more Hmg-CoA reductase inhibitors comprising one or more statin pharmacological agents, to a desired dosage of about 1.1 milligrams to about 1.2 milligrams of the one or more Hmg-CoA reductase inhibitors per kilogram bodyweight of the mammal over of period of about fourteen days;
   c) administering one or more interferons, other than a gamma interferon, in a dosage of about 60,000 international units to about 70,000 international units per kilogram of bodyweight of the mammal three times per week after reaching the desired dosage of the one or more Hmg-CoA reductase inhibitors; and
   d) continuing the administration of the one or more Hmg-CoA reductase inhibitors and the one or more interferons to treat the melanoma and reduce the likelihood of death by the melanoma greater than by either the one or more Hmg-CoA reductase inhibitors or the one or more interferons administered alone.

22. The method claim 21 further comprising the administration of about 200 micrograms of selenium and of from about 600 milligrams to about 1200 milligrams of calcium to the mammal.

23. The method of claim 21 further comprising:
e) administering a maintenance dosage of from about 0.7 milligrams to about 1.0 milligrams of the one or more Hmg-CoA reductase inhibitors per kilogram of the bodyweight of the mammal per day and a dosage of from about 60,000 international units to about 70,000 international units per kilogram of the body weight of the mammal of the one or more interferons once per week.

24. The method of claim 23 wherein step e) further comprises a dosage of about 200 micrograms of selenium per day.

25. The method of claim 23 wherein step e) further comprises a dosage of from about 600 milligrams to about 1200 milligrams of calcium per day.

26. The method of claim 24 further comprising:
f) reducing the maintenance dosage of the one or more Hmg-CoA reductase inhibitors to about 35,000 international units to about 45,000 international units per kilogram of the bodyweight of the mammal after a period of about one year of absence of the metastatic melanoma.

27. A method of treating a mammal having cancer, said method comprising regressing cancer through the administration of a therapeutically effective amount of one or more Hmg-CoA reductase inhibitors, the one or more Hmg-CoA reductase inhibitors comprising one or more statin pharmacological agents and a therapeutically effective amount of one or more interferons, other than gamma interferons, wherein said Hmg-CoA reductase inhibitors and interferons are administered to treat said cancer and reduce the likelihood of death caused by said cancer greater than by either the one or more Hmg-CoA reductase inhibitors or the one or more interferons administered alone.

28. The method of claim 27, wherein the one or more interferons comprise an alpha-type interferon.

29. The method of claim 27, wherein the one or more interferons comprise interferon alpha-2b.

30. A method of treating a mammal having cancer, said method comprising cytocidally effecting cancer cells through the administration of a therapeutically effective amount of one or more Hmg-CoA reductase inhibitors, the one or more Hmg-CoA reductase inhibitors comprising one or more statin pharmacological agents, and a therapeutically effective amount of one or more interferons, other than gamma interferons, wherein said one or more Hmg-CoA reductase inhibitors and one or more interferons are administered to treat said cancer and reduce the likelihood of death caused by said cancer greater than by either the one or more Hmg-CoA reductase inhibitors or the one or more interferons administered alone.

31. A method of treating cancer of a mammal, said method comprising:
the administration of a therapeutically effective amount of one or more Hmg-CoA reductase inhibitors, the one or more Hmg-CoA reductase inhibitors comprising one or more statin pharmacological agents, and a therapeutically effective amount of one or more interferons, the one or more interferons selected from the interferon alfa-2a, alfa-2b, alfa-2c, alfa-n1, alfa-n3, beta interferon, pharmacologically similar interferons, and combinations thereof; and
the combination of the therapeutically effective amounts of one or more Hmg-CoA reductase inhibitors and one or more interferons providing at least a partial response to the cancer of the mammal.

32. The method of claim 31 further comprising the combination of the therapeutically effective amounts of one or more Hmg-CoA reductase inhibitors and one or more interferons providing a complete response to the cancer of the mammal.

33. The method of claim 31 wherein the one or more Hmg, CoA reductase inhibitors is chosen from lovastatin, simvastatin, pravastatin, fluvastatin, atorvastatin, cerivastatin, combinations thereof and any statin pharmacological agents.

34. A method of treating cancer of a mammal, said method comprising:
the administration of a therapeutically effective amount of one or more Hmg-CoA reductase inhibitors, the one or more Hmg-CoA reductase inhibitors comprising one or more statin pharmacological agents, and a therapeutically effective amount of one or more interferons, other than gamma interferons; and
the combination of the therapeutically effective amounts of one or more Hmg-CoA reductase inhibitors and one or more interferons stabilizing the cancer of the mammal.

35. The method of claim 34 wherein the one or more Hmg-CoA reductase inhibitors is chosen from lovastatin, simvastatin, pravastatin, fluvastatin, atorvastatin, cerivastatin, combinations thereof and any statin pharmacological agents.

36. A method of treating a mammal having cancer, comprising the steps of:
a) providing a mammal having cancer;
b) administering a gradually increasing dosage of a one or more Hmg-CoA reductase inhibitors to the mammal until the dosage of the one or more Hmg-CoA reductase inhibitors reaches a desired dosage of the one or more Hmg-CoA reductase inhibitors based upon the bodyweight of the mammal, the one or more Hmg-CoA reductase inhibitors comprising one or more statin pharmacological agents;
c) administering one or more interferons, other than a gamma interferon, in a dosage based upon the bodyweight of the mammal after reaching the desired dosage of the one or more Hmg-CoA reductase inhibitors; and
d) continuing the administration of the one or more Hmg-CoA reductase inhibitors and the one or more interferons to cause at least a partial response to the mammal's cancer.

37. The method of claim 36 wherein step d) further comprises continuing the administration of the one or more Hmg-CoA reductase inhibitors and the one or more interferons to cause a complete response to the mammal's cancer.

38. A method of treating a mammal having cancer, comprising the steps of:
a) providing a mammal having cancer;
b) administering a gradually increasing dosage of one or more Hmg-CoA reductase inhibitors to the mammal until the dosage of one or more Hmg-CoA reductase inhibitors reaches a desired dosage of the one or more Hmg-CoA reductase inhibitors based upon the bodyweight of the mammal, the one or more Hmg-CoA reductase inhibitors comprising one or more statin pharmacological agents;
c) administering one or more interferons, other than a gamma interferon, in a dosage based upon the bodyweight of the mammal after reaching the desired dosage of the one or more Hmg-CoA reductase inhibitors; and
d) continuing the administration of the one or more Hmg-CoA reductase inhibitors and the one or more interferons to cause the mammal's cancer to be stable.

* * * * *